US005646151A

United States Patent [19]

Kruse et al.

[11] Patent Number: 5,646,151
[45] Date of Patent: Jul. 8, 1997

[54] KAPPA AGONIST COMPOUNDS AND PHARMACEUTICAL FORMULATIONS THEREOF

[75] Inventors: Lawrence L Kruse, Haddonfield, N.J.; Virendra Kumar, Paoli, Pa.; An-Chih Chang, Phoenixville, Pa.; Diane L. DeHaven-Hudkins; John J. Farrar, both of Chester Springs, Pa.; Alan L. Maycock, Malvern, Pa.

[73] Assignee: Adolor Corporation, Malvern, Pa.

[21] Appl. No.: 612,680

[22] Filed: Mar. 8, 1996

[51] Int. Cl.[6] ............ A61K 31/495; C07D 241/04
[52] U.S. Cl. ............ 514/255; 544/337; 544/358; 544/359; 544/360; 544/372; 544/383; 544/386; 544/387; 544/389; 514/85
[58] Field of Search ............... 514/255; 544/337, 544/358, 359, 360, 372, 383, 386, 387, 389

[56] References Cited

U.S. PATENT DOCUMENTS

| 4,065,573 | 12/1977 | Lednicer | 424/278 |
|---|---|---|---|
| 4,098,904 | 7/1978 | Szmuszkovicz | 424/324 |
| 4,145,435 | 3/1979 | Szmuszkovicz | 424/274 |
| 4,212,878 | 7/1980 | Lednicer et al. | 424/274 |
| 4,359,476 | 11/1982 | Kaplan et al. | 424/274 |
| 4,438,130 | 3/1984 | Kaplan | 424/274 |
| 4,663,343 | 5/1987 | Horwell et al. | 514/429 |
| 4,855,316 | 8/1989 | Horwell et al. | 514/422 |
| 4,906,655 | 3/1990 | Horwell et al. | 514/422 |

FOREIGN PATENT DOCUMENTS

| 0 147 085 | 12/1984 | European Pat. Off. . |
|---|---|---|
| 0 233 793 | 1/1987 | European Pat. Off. . |
| 0 372 466 | 6/1988 | European Pat. Off. . |
| 0 330 461 | 2/1989 | European Pat. Off. . |
| 0 330 467 | 2/1989 | European Pat. Off. . |
| 0 366 327 | 10/1989 | European Pat. Off. . |
| 0207 773 | 6/1986 | WIPO . |
| WO 92/20657 | 5/1992 | WIPO . |

*Primary Examiner*—Joseph McKane

[57] ABSTRACT

Compounds, compositions and method of treating hyperalgesia comprising a compound of formula I, II, III and IV as defined in the specification.

10 Claims, No Drawings

KAPPA AGONIST COMPOUNDS AND PHARMACEUTICAL FORMULATIONS THEREOF

BACKGROUND OF THE INVENTION

1. Field of the Invention

This invention relates to compounds, to processes of their preparation, to pharmaceutical compositions containing them and to their medical use as agonists at kappa opioid receptors.

2. Reported Developments

Opium and its derivatives are potent analgesics that also have other pharmacological effects, and exert their effects by interacting with high-affinity receptors. It has been shown by investigators that there are at least three major opioid receptor types in the central nervous system (hereinafter CNS) and in the periphery. These receptors, known as mu (μ), delta (δ) and kappa (κ), have distinct pharmacological profiles, anatomical distributions and functions. [See, for example: Wood, P. L., Neuropharmacology, 21, 487–497, 1982; Simon, E. J., Med. Res. Rev., 11, 357–374, 1991; Lutz et at, I. Recept. Res. 12, 267–286; and Mansour et at, Opioid I, ed. Hem,. A. (Springer, Berlin) pp. 79–106, 1993.] The δ receptors are abundant in CNS and mediate analgesia, gastrointestinal motility and various hormonal functions. The μ receptors bind morphine-like drugs and mediate the opiate phenomena associated with morphine, including analgesia, opiate dependence, cardiovascular and respiratory functions, and several neuroendocrine effects.

The κ receptors have a wide distribution in CNS and mediate a spectrum of functions including the modulation of drinking, water balance, food intake, gut motility, temperature control and various endocrine functions. They also produce analgesia. [See, for example: Leander et at, J. Pharmacol. Exp. Ther. 234, 463–469, 1985; Morley et at, Peptides 4, 797–800, 1983; Manzanares et al, Neuroendocrinology 52, 200–205, 1990; and Iyengar et at, J. Pharmacol. Exp. Ther, 238, 429–436, 1986.]

Most clinically used opioid analgesics such as morphine and codeine act as μ receptor agonists. These opioids have well-known, undesirable and potentially dangerous dependence forming side effects. Compounds which are κ-receptor agonists act as analgesics through interaction with κ opioid receptors. The advantage of these agonists over the classical μ receptor agonists, such as morphine, lies in their ability to cause analgesia while being devoid of morphine-like behavioral effects and addiction liability.

A large number of classes of compounds which act as agonists at κ opioid receptors have been described in the art including the following illustrative classes of compounds.

U.S. Pat. No. 4,065,573 discloses 4-amino-4-phenylcyclohexane ketal compounds having analgesic activity.

U.S. Pat. No. 4,212,878 discloses phenylacetamide derivatives having analgesic properties and reduced physical dependence liability properties, relative to morphine and methadone.

U.S. Pat. No. 4,145,435 discloses N-(2-aminocycloaliphatic)-phenylacetamide compounds having analgesic activity and narcotic antagonist activity.

U.S. Pat. No. 4,098,904 discloses N-(2-aminocycloaliphatic)-benzoamides and naphthamides useful for relieving pain.

U.S. Pat. No. 4,359,476 discloses substituted cycloalkane-amides useful as analgesic and having low abuse liability.

U.S. Pat. No. 4,438,130 discloses 1-oxa-, aza- and thiaspirocyclic compounds having analgesic activity, low physical dependence and abuse liability properties and little dysphoric inducing properties.

U.S. Pat. No. 4,663,343 discloses substituted naphthalenyloxy-1,2-diaminocyclohexyl amides as analgesics.

U.S. Pat. No. 4,906,655 discloses 1,2-cyclohexylaminoaryl amides having high kappa-opioid affinity, selectivity and potency and useful as analgesics, diuretics, anti-inflammatory and psychotherapeutic agents.

SUMMARY OF THE INVENTION

Compounds having kappa opioid agonist activity, compositions containing them and method of using them as analgesics are provided.

In its compound aspect, the present invention provides a compound of the formulae I, II, III and IV, or a pharmaceutically acceptable salt thereof.

The compounds of formula (I) have the following structure:

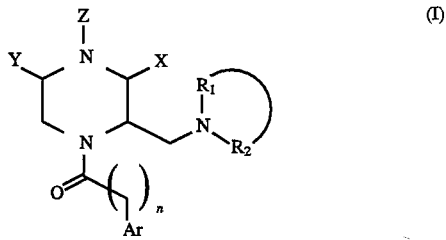

(I)

wherein n=1–3, where n=1 is preferred $R_1$ and $R_2$ are independently=$CH_3$; —$(CH_2)_m$, where m=4–8, m=4 is most preferred; —$CH_2CH(OH)(CH_2)_2$—; —$CH_2CH(F)(CH_2)_2$—; —$(CH_2)_2O(CH_2)_2$—; or —$(CH_2)_2CH=CHCH_2$—;

Ar=unsubstituted or mono-, or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

Z is

—$P(O)(OBn)_2$; —$P(O)(OH)_2$; —$(CH_2)_pC(O)NHOH$; —$(CH_2)_pCO_2H$; —$SO_2CH_3$; —$SO_2NH_2$; —$CO(CH_2)_pCH(NH_2)(CO_2H)$; —$COCH(NH_2)(CH_2)_pCO_2H$; —$CO_2CH_3$; —$CONH_2$; —$(CH_2)_pO(CH_2)_pCO_2H$; —$(CH_2)_pO(CH_2)_pCONHOH$; —$(CH_2)_pNHSO_2CH_3$; —$(CH_2)_pNHC(S)NHCH(CO_2H)(CH_2)_pCO_2H$; —$(CH_2)_pSO_3H$; or

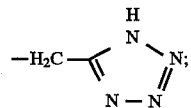

or Z is

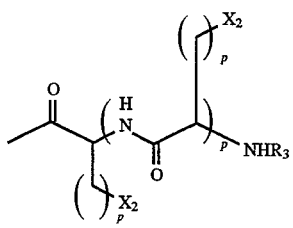

wherein p=0–20;

$R_3$=—H or —Ac;

$X_2$=—$CO_2H$; —$NHSO_2CH_3$; NHP(O)(OBn)$_2$; NHP(O)(OH)$_2$; —OP(O)(OBn)$_2$; or OP(O)(OH)$_2$;

X and Y are independently

—$CH_2NHSO_2CH_3$, —$CH_2NHP(O)(OBn)_2$, —$CH_2NHP(O)(OH)_2$, —$CH_2OP(O)(OBn)_2$, —$CH_2OP(O)(OH)_2$, —$(CH_2)_qO(CH_2)_qCO_2H$, —$(CH_2)_qO(CH_2)_qSO_3H$, —$(CH_2)_qO(CH_2)_qCHNHOH$, —$CH_2NHC(S)NHCH(CO_2H)(CH_2)_qCO_2H$ or

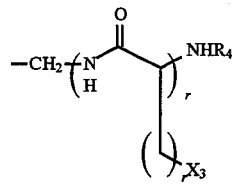

wherein r=1–20

$R_4$=—H or —Ac $X_3$=—$CO_2H$; —$NHSO_2CH_3$; —NHP(O)(OBn)$_2$; —NHP(O)(OH)$_2$; —OP(O)(OBn)$_2$; or —OP(O)(OH)$_2$

The compounds of formula II have the following structure:

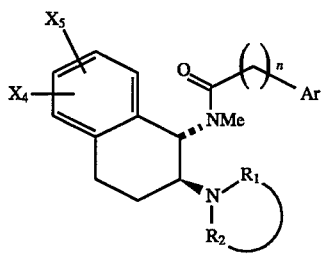

(II)

wherein n=1–3, where n=1 is preferred $R_1$ and $R_2$ are independently=$CH_3$; —$(CH_2)_m$, where m=4–8, m=4 is most preferred; —$CH_2CH(OH)(CH_2)_2$—; —$CH_2CH(F)(CH_2)_2$—; —$(CH_2)_2O(CH_2)_2$—; or —$(CH_2)_2CH=CHCH_2$—;

Ar=unsubstituted or mono-, or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

$X_4$ and $X_5$ are independently

—OP(O)(OBn)$_2$; —OP(O)(OH); —$CO_2H$; —$SO_3H$; —$SO_3H$; —O$(CH_2)_nCO_2H$; —$NHSO_2CH_3$; —CONH$(CH_2)_sCO_2H$; or —$SO_2NH(CH_2)_sCO_2H$; wherein s=1–5 or $X_4$ and $X_5$ are independently

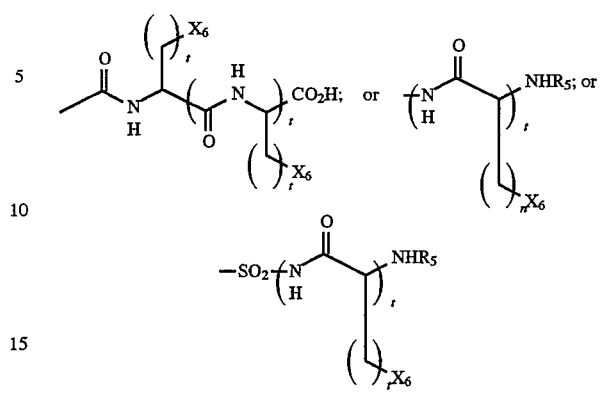

wherein t=1–20

$R_5$=—H or —Ac $X_6$=—$CO_2H$; —$NHSO_2CH_3$; —NHP(O)(OBn)$_2$; —NHP(O)(OH)$_2$; —OP(O)(OBn)$_2$; or —OP(O)(OH)$_2$.

The compounds of formula III have the following structure:

(III)

wherein n=1–3, where n=1 is preferred $R_1$ and $R_2$ are independently=$CH_3$; —$(CH_2)_m$, where m=4–8, m=4 is most preferred; —$CH_2CH(OH)(CH_2)_2$—; —$CH_2CH(F)(CH_2)_2$; —$(CH_2)_2O(CH_2)_2$—; or —$(CH_2)_2CH=CHCH_2$—;

Ar=unsubstituted or mono-, or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

$X_7$ is

—$NHSO_2CH_3$; —NHP(O)(OBn)$_2$; —NHP(O)(OH)$_2$; —$(CH_2)_uNHSO_2CH_3$; —$(CH_2)_uNHC(S)NHCH(CO_2H)(CH_2)_uCO_2H$; —CONHOH; or —$(CH_2)_uCONHOH$;

wherein u=1–5 or X₇ is

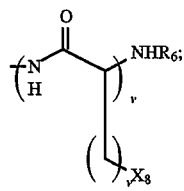

R₆= —H or —Ac
X₈= —CO₂H; —NHSO₂CH₃; —NHP(O)(OBn)₂;
—NHP(O)(OH)₂; —OP(O)(OBn)₂; or
—OP(O)(OH)₂;

or

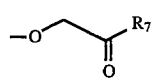

R₇= —NH(CH₂)ᵥCO₂H; —NH(CH₂)ᵥCH(NH₂)(CO₂H);
—NHCH(CO₂H)(CH₂)ᵥNH₂; —NH(CH₂)ᵥSO₃H;
—NH(CH₂)ᵥPO₃H₂; —NH(CH₂)ᵥNHC(NH)NH₂; or
—NHCH(CO₂H)(CH₂)ᵥCO₂H; and
v = 1–20.

The compounds of formula IV have the following structure:

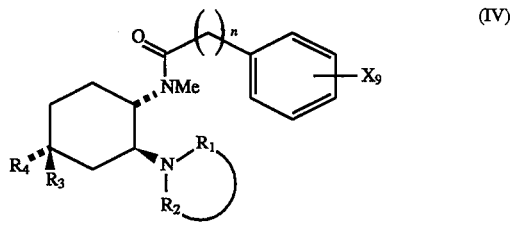
(IV)

wherein n=1–3, where n=1 is preferred

R₁ and R₂ are independently=CH₃; —(CH₂)ₘ, where m=4–8, m=4 is most preferred;
—CH₂CH(OH)(CH₂)₂—; —CH₂CH(F)(CH₂)₂—;
—(CH₂)₂O(CH₂)₂—; or —(CH₂)₂CH=CHCH₂—;

R₃ and R₄ are independently H; OCH₃; alkyl; or —O(CH₂)₂;

X₉=1–4 substituents selected from the groups consists of

—halogen; —CF₃; —OCH₃; —SO₂NH(CH₂)qCO₂H;
—CONH(CH₂)qCO₂H; —NH₂; —NHSO₂CH₃;
—NHP(O)(OBn)₂; —NHP(O)(OH)₂; —SO₂CH₃;
—OP(O)(OBn)₂; —OP(O)(OH)₂; —CO₂H;
—O(CH₂)qCO₂H; —O(CH₂)qSO₃H,
—O(CH₂)qOPO₃H₂; wherein
q=1–20.

or X₉ is

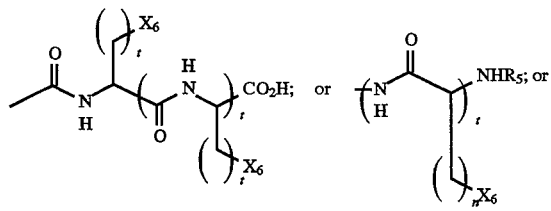

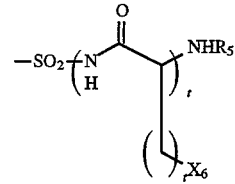

wherein t=1–20

R₅=—H or —Ac

X₆=—CO₂H; —NHSO₂CH₃; —NHP(O)(OBn)₂; —NHP(O)(OH)₂; —OP(O)(OBn)₂; or —OP(O)(OH)₂.

DETAILED DESCRIPTION OF THE INVENTION

Peripherally-acting κ agonists can be prepared by the attachment of polar groups to non-peptide κ opioid receptor selective agonists, such as the arylacetamides. In designing the peripherally-acting ligands, the introduction of the polar groups may result in either retention or enhancement of antinociceptive potency and selectivity and also may increase the polarity of the ligand sufficient to reduce or eliminate CNS penetration across the blood-brain barrier (BBB). Thus, the identity and the positioning of the polar group(s) are important.

Using the prototypic arylacetamide, U50,488, as an example, the arylacetamide pharmacophore can be divided into three regions: the aromatic region, the central region, and the amine region. All three regions represent potential positions for the attachment of polar groups.

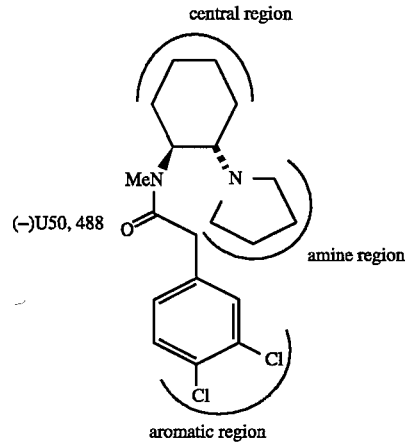

Compounds of formula (I) of the present invention are made as follows.

A series of novel compounds were made based on the class of arylacetamides reported by Glaxo (J. Med. Chem. 1993, 36, 2075). Specifcally, compound 1 can be deprotected to yield intermediate 2, which can be derivatized by the attachment of a variety of polar groups (Scheme 1).

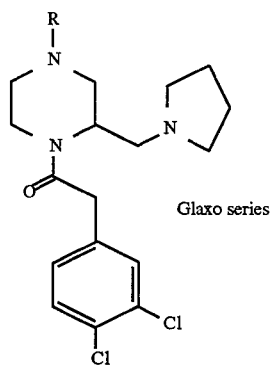

Glaxo series

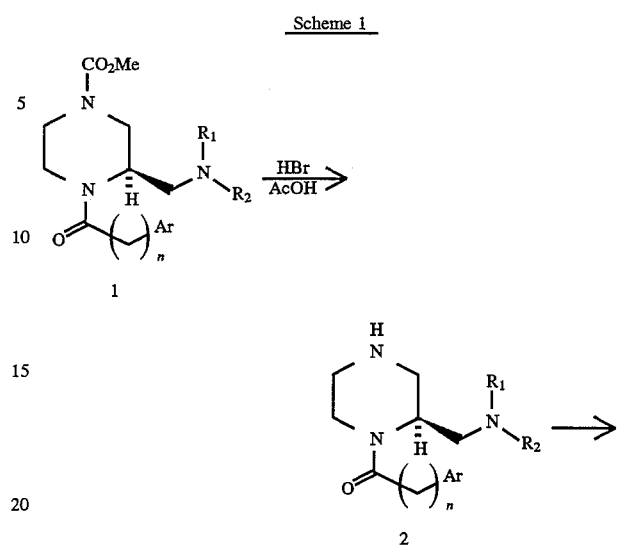

Scheme 1

Analogs shown in formula I.

wherein Ar, $R_1$, $R_2$, and n are defined in formula I.

The 3'-substituted series can be prepared via Scheme 2. The reduction of the Schiff base intermediate formed during the cyclization to 6 is expected to be stereoselective due to the directing effect of the neighboring hydroxymethyl group. Both intermediates 11 and 12 can be derivatized to coffer peripheral selectivity.

The 5'-substituted series can be prepared via Schemes 3 and 4. Starting from N-t-Boc-O-MEM-D-serine, the 5'-(S) series can be prepared, and starting from from N-t-Boc-O-MEM-L-serine allows the preparation of the 5'-(R) series.

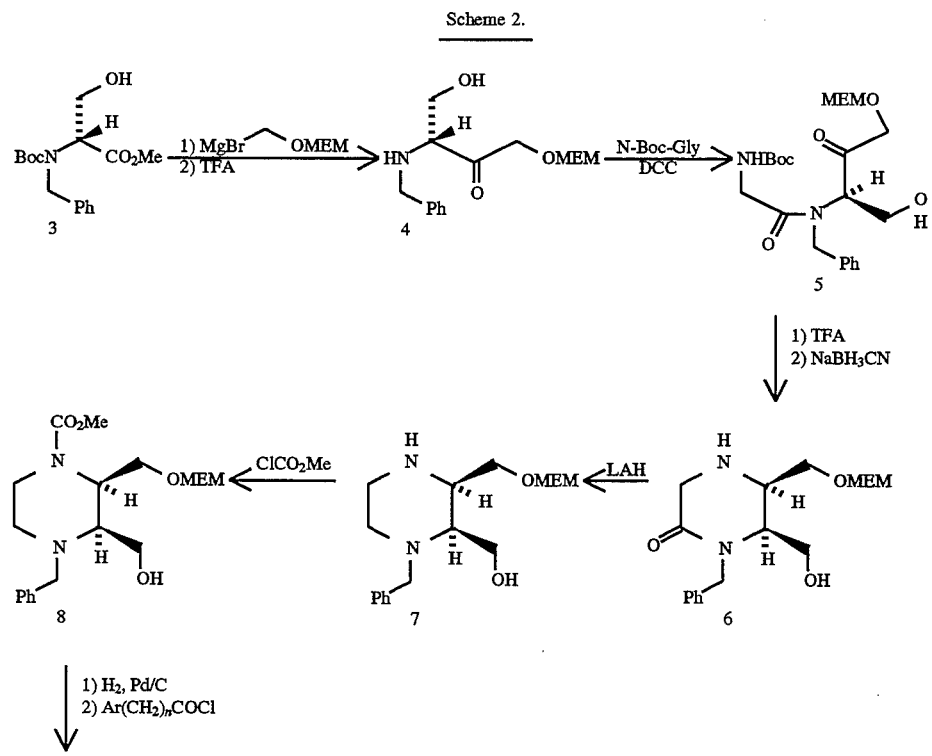

5,646,151
-continued
Scheme 2.
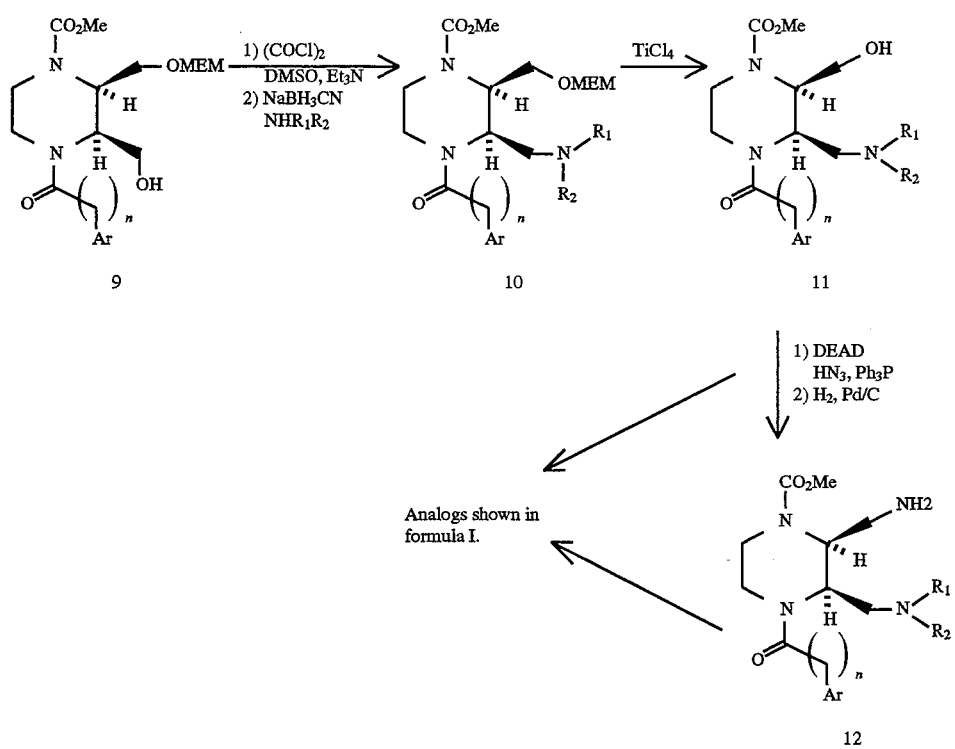
wherein Ar, $R_1$, $R_2$, and n are as defined in formula I.
Scheme 3.
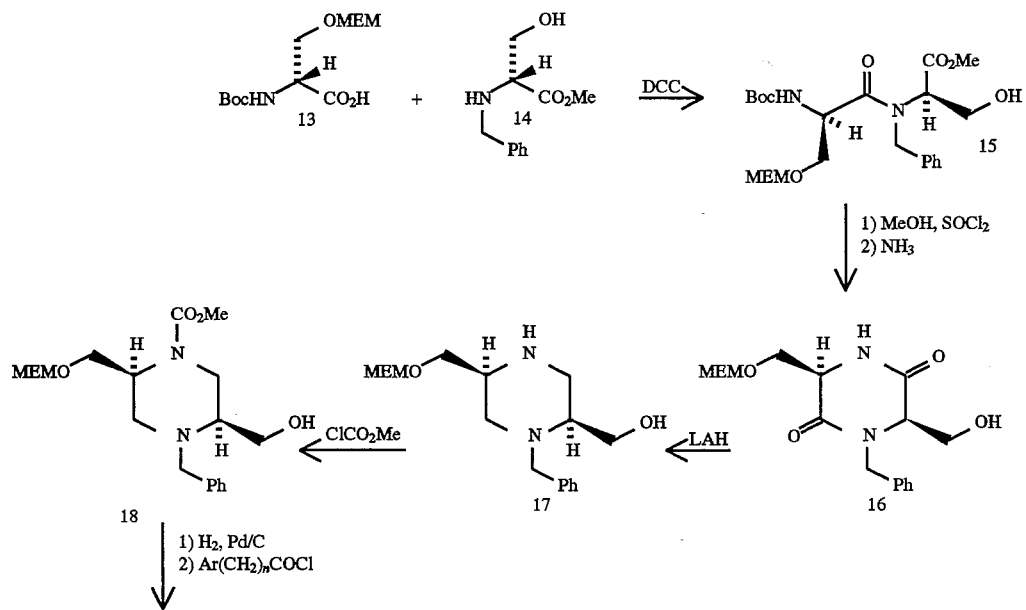

-continued
Scheme 3.
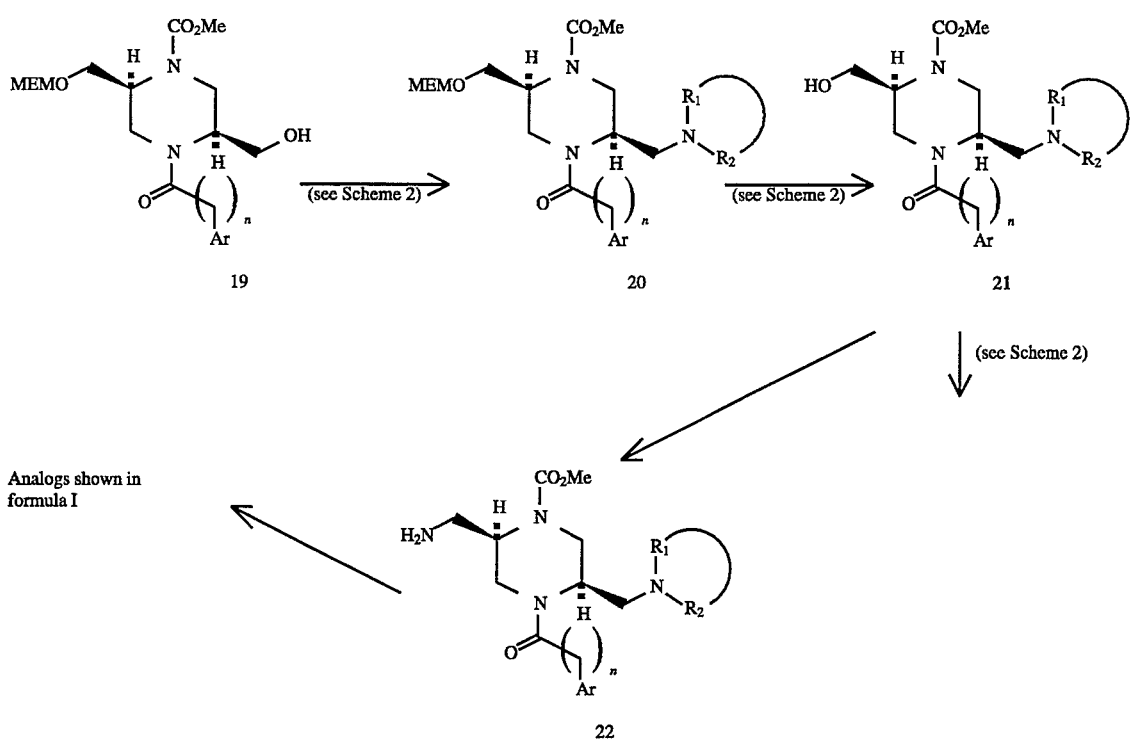
wherein Ar, $R_1$, $R_2$, and n are as defined in formula I.
Scheme 4.
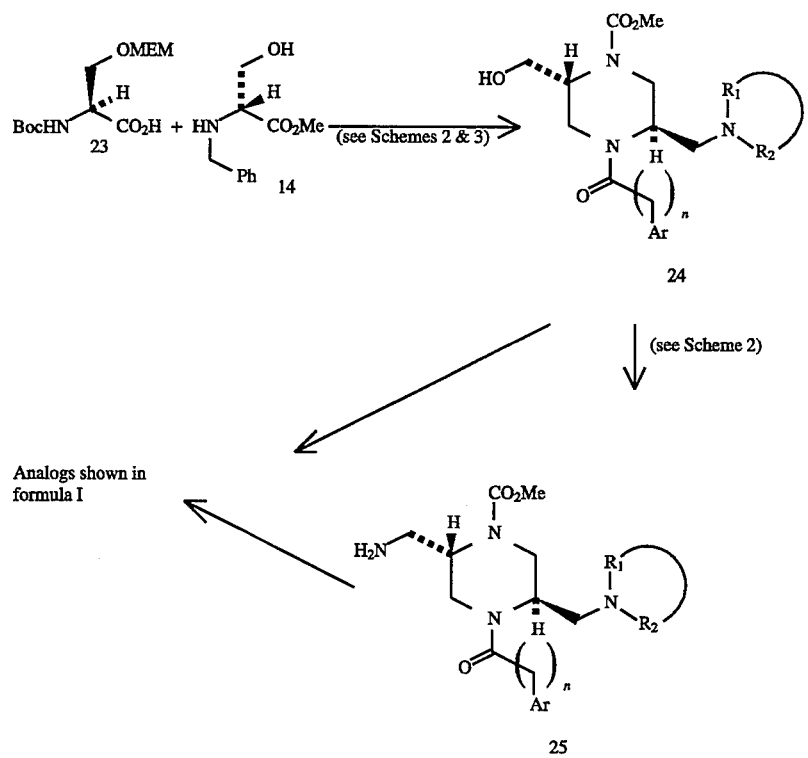

Using Schemes 1-4 the following example compounds are made.

Intermediate 3 can be treated with t-butyl bromoacetate and deprotected to produce {4-[1-(3,4-Dichlorophenyl)acetyl-2R-(1-pyrrolidinyl)-methyl]piperazinyl}acetic acid (26).

Intermediate 3 can be reacted with methane sulfonyl chloride to produce [1-(3,4-Dichlorophenyl)acetyl-4-methanesulfonyl-2R-(1-pyrrolidinyl)methyl]piperazine (27).

Intermediate 3 can be coupled to N-t-Boc-L-aspartic acid-β-benzyl ester and deprotected to produce [4-S-Aspartic acid-a-amido-1-(3,4-dichlorophenyl)acetyl-2R-(1-pyrrolidinyl)methyl]piperazine (28).

Intermediate 11 can be treated with t-butyl bromoacetate and deprotected to produce Methyl-[2R-(O-2-acetic acid)hydroxymethyl-4-(3,4-dichlorophenyl)acetyl-3R-(1-pyrrolidinyl)methyl]-1-piperazinecarboxylate (29).

Intermediate 11 can be coupled to to N-t-Boc-L-aspartic acid-b-benzyl ester and deprotected to produce Methyl-[2R-(O-S-aspartic acid-a-acetyl)hydroxymethyl-4-(3,4-dichlorophenyl)acetyl-3R-(1-pyrrolidinyl)methyl]-1-piperazinecarboxylate (30).

Intermediate 12 can be treated with methanesulfonyl chloride to produce Methyl-[4-(3,4-dichlorophenyl) acetyl-2R-(N-methanesulfonamido)aminomethyl-3R-(1-pyrrolidinyl)methyl]-1-piperazinecarboxylate (31).

Intermediate 12 can be coupled to 2S-isothiocyanato-succinic acid-dibenzyl ester and deprotected to yield Methyl-{4-[3,4-dichlorophenyl]acetyl-3R-[1-pyrrolidinyl]methyl-2R-[N-(succinic acid-2S-thioureido)]aminomethyl}-1-piperazinecarboxylate (32).

Intermediate 21 can be treated with t-butyl bromoacetate and deprotected to produce Methyl-[2S-(O-2-acetic acid)hydroxymethyl-4-(3,4-dichlorophenyl)acetyl-5R-(1-pyrrolidinyl)methyl]-1-piperazinecarboxylate (33).

Intermediate 21 can be coupled to to N-t-Boc-L-aspartic acid-b-benzyl ester and deprotec ted to produce Methyl-[2S-(O-S-aspartic acid-a-acetyl)hydroxymethyl-4-(3,4-dichlorophenyl)acetyl-5R-(1-pyrrolidinyl)methyl]-1-piperazinecarboxylate (34).

Intermediate 22 can be treated with methanesulfonyl chloride to produce Methyl-[4-(3,4-dichlorophenyl)acetyl-2S-(N-methanesulfonamido)aminomethyl-5R-(1-pyrrolidinyl)methyl]-1-piperazinecarboxylate (35).

Intermediate 22 can be coupled to 2S-isothiocyanato-succinic acid-dibenzyl ester and deprotected to yield Methyl-{4-[3,4-dichlorophenyl]acetyl-5R-[1-pyrrolidinyl]methyl-2S-[N-(succinic acid-2S-thioureido)]aminomethyl}-1-piperazinecarboxylate (36).

The 2R isomers of 33-34 and 35-36 can be prepared from intermediates 24 and 25, respectively to produce Methyl-[2R-(O-2-acetic acid)hydroxymethyl-4-(3,4-dichlorophenyl)acetyl-5R-(1-pyrrolidinyl)methyl]-1-piperazinecarboxylate (37).

Methyl-[2R-(O-S-aspartic acid-a-acetyl)hydroxymethyl-4-(3,4-dichlorophenyl)acetyl-5R-(1-pyrrolidinyl)methyl]-1-piperazinecarboxylate (38).

Methyl-[4-(3,4-dichlorophenyl)acetyl-2R-(N-methanesulfonamido)aminomethyl-5R-(1-pyrrolidinyl)methyl]-1-piperazinecarboxylate (39).

Methyl-{4-[3,4-dichlorophenyl]acetyl-5R-[1-pyrrolidinyl]methyl-2R-[N-(succinic acid-2S-thioureido)]aminomethyl}-1-piperazinecarboxylate (40).

The corresponding structural formulas are shown hereunder.

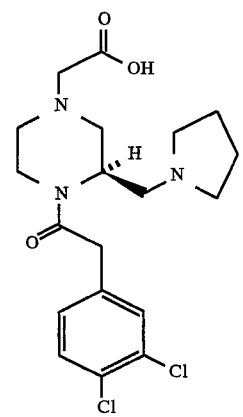

26

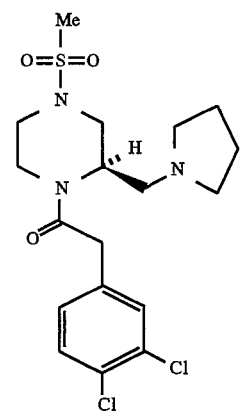

27

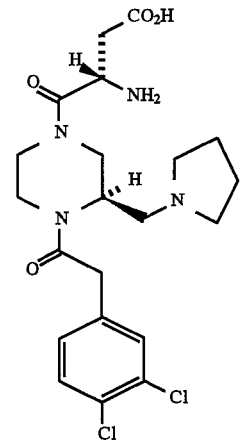

28

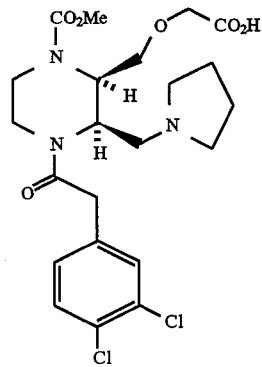

29

30
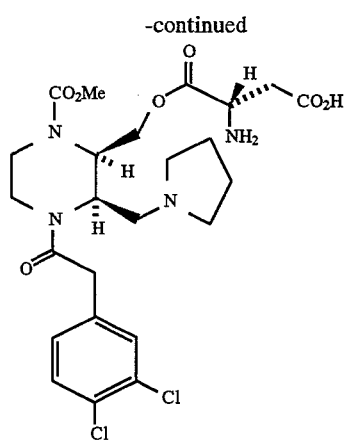
31
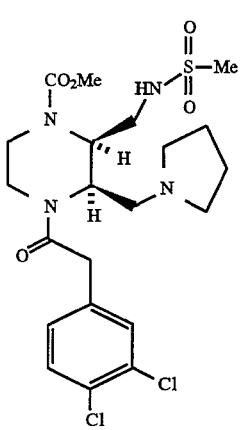
32
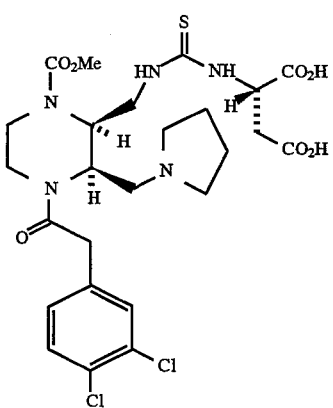
33
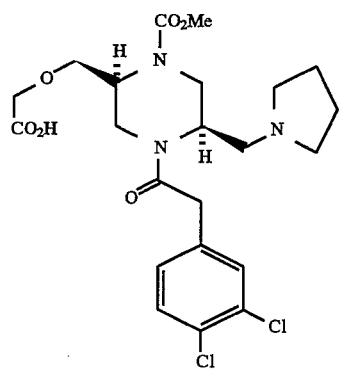
34
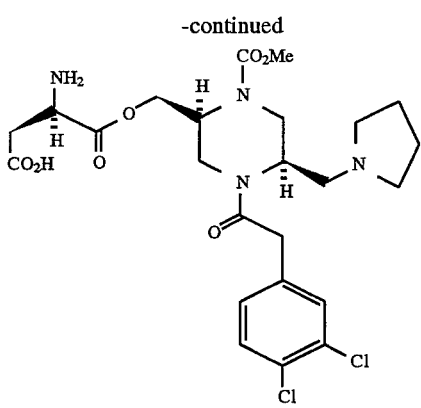
35
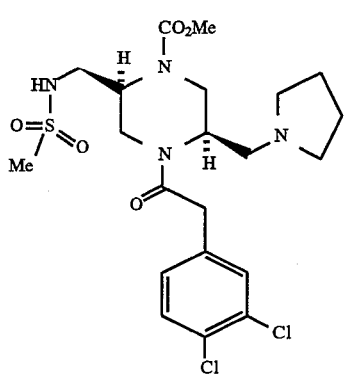
36
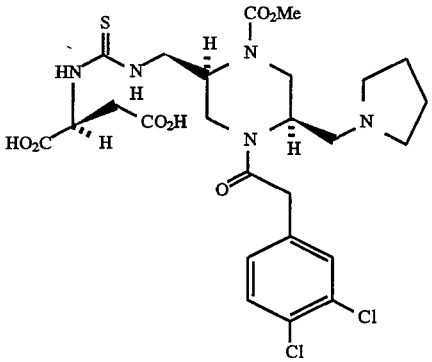
37
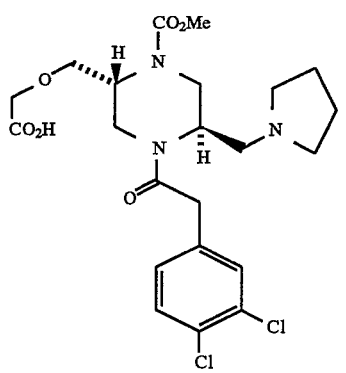

17

-continued

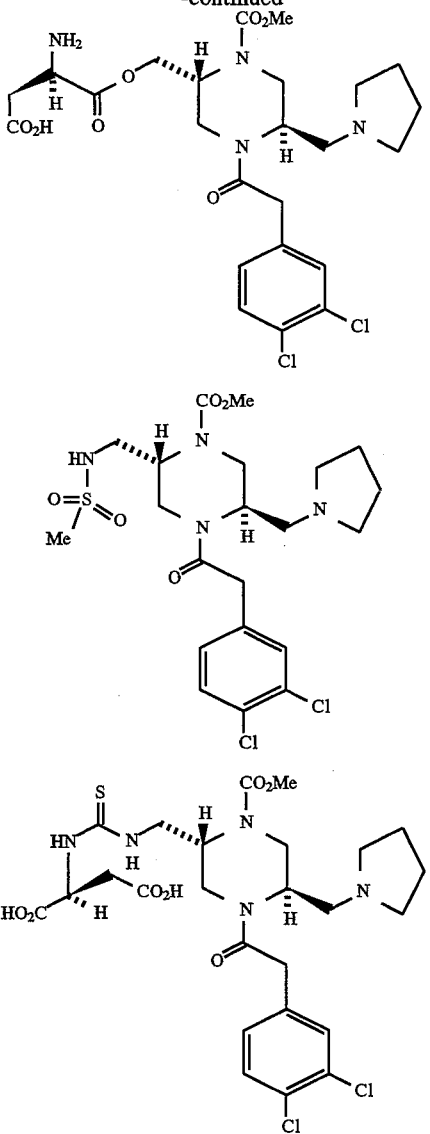

18

Compounds of formula II of the present invention are made by peripheralization by substitutions of the benzo portion of the tetrahydronaphthyl ring of DuPont series of compounds with polar groups.

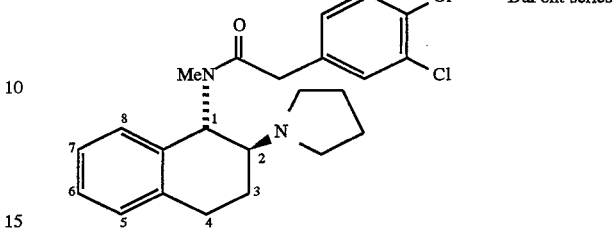

DuPont series

Starting material or precursors of the starting material are commercially available and thus allows regiospecific substitutions of the tetrahydronaphthyl ring (Scheme 5). While 5-hydroxytetralone, 6-hydroxytetralone, 7-hydroxytetralone, and 7-aminotetralone derivatives are readily available, 5-aminotetralone could be prepared from 5-hydroxytetralone (J. Org. Chem. 1972, 37, 3570).

The tetralone derivatives can be converted to dihydronaphthyl derivatives and subjected to chemistry similar to that employed in the preparation of U50,488 derivatives. The resulting compounds are racemic mixtures that can be derivatized to confer peripheral selectivity. If necessary, the final compounds or one of the intermediates can be resolved to test both enantiomers.

Scheme 5.

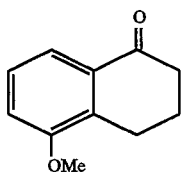
41

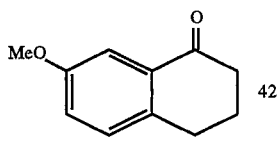
42

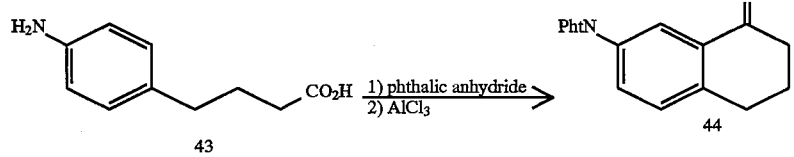

-continued
Scheme 5.
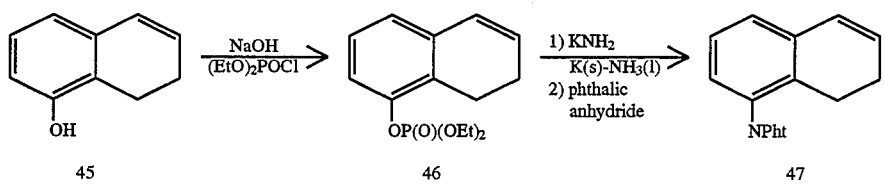
Scheme 6.
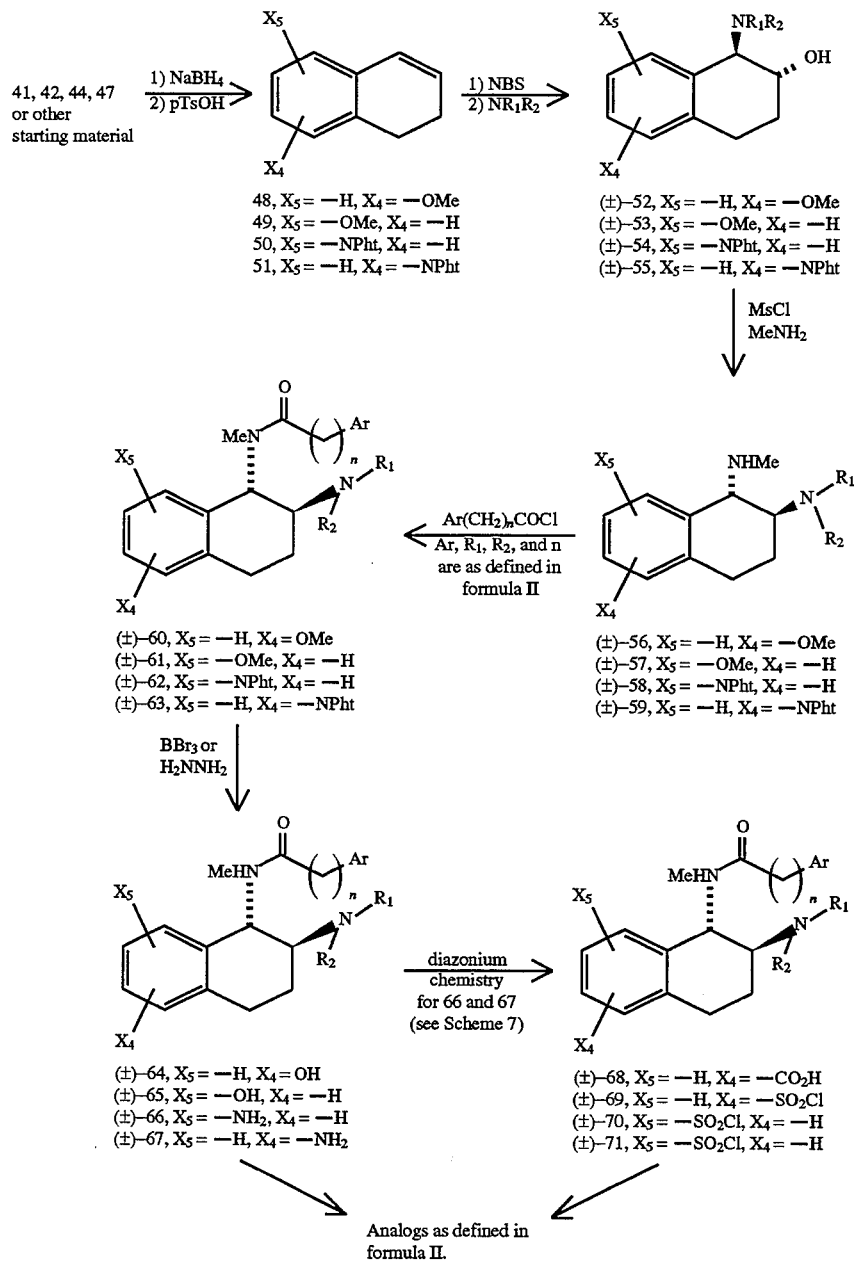

Scheme 7.

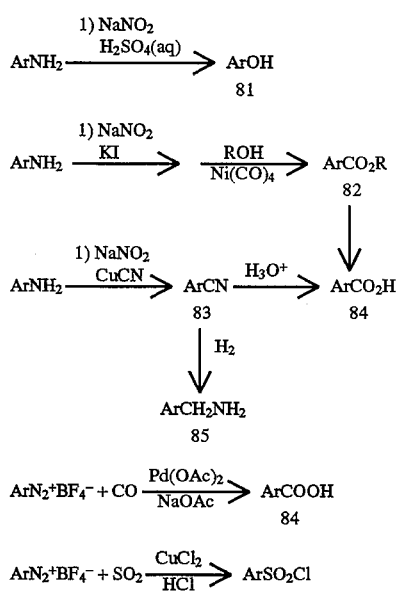

81, 82, 84, 85, 86 ⟶ Analogs shown in formulas II–IV

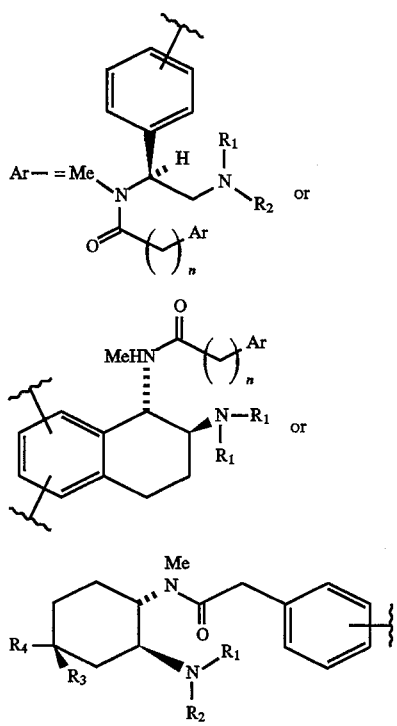

wherein $R_1$, $R_2$, and n are as defined in formula I.

Following the procedure shown in Schemes 5–7, the following example compounds are prepared.

Intermediate (±)-64 can be treated with t-butyl bromoacetate and deprotected to produce (±)-2-(3,4-dichlorophenyl)-N-methyl-N-1-[1,2,3,4-tetrahydro-5-(O-2-acetic acid)-hydroxy-2-(1-pyrrolidinyl)naphthyl]acetamide (72).

Intermediate (±)-65 can be treated with t-butyl bromoacetate and deprotected to produce (±)-2-(3,4-dichlorophenyl)-N-methyl-N-1-[1,2,3,4-tetrahydro-7-(O-2-acetic acid)-hydroxy-2-(1-pyrrolidinyl)naphthyl]acetamide (73).

Intermediate (±)-66 can be treated with methanesulfonyl chloride to produce (±)-2-(3,4-dichlorophenyl)-N-methyl-N-1-[1,2,3,4-tetrahydro-7-(N-methanesulfonamido)-amino-2-(1-pyrrolidinyl)naphthyl]acetamide (74).

Intermediate (±)-67 can be treated with methanesulfonyl chloride to produce (±)-2-(3,4-dichlorophenyl)-N-methyl-N-1-[1,2,3,4-tetrahydro-5-(N-methanesulfonamido)-amino-2-(1-pyrrolidinyl)naphthyl]acetamide (75).

Intermediate (±)-68 can be treated with glycine benzyl ester and deprotected to produce (±)-2-(3,4-dichlorophenyl)-N-methyl-N-1-[1,2,3,4-tetrahydro-5-(N-2-acetic acid)-carboxamido-2-(1-pyrrolidinyl)naphthyl]acetamide (76).

Intermediate (±)-69 can be treated with glycine benzyl ester and deprotected to produce (±)-2-(3,4-dichlorophenyl)-N-methyl-N-1-[1,2,3,4-tetrahydro-5-(N-2-acetic acid)-sulfonamido-2-(1-pyrrolidinyl)naphthyl]acetamide (77).

Intermediate (±)-70 can be treated with glycine benzyl ester and deprotected to produce (±)-2-(3,4-dichlorophenyl)-N-methyl-N-1-[1,2,3,4-tetrahydro-7-(N-2-acetic acid)-carboxamido-2-(1-pyrrolidinyl)naphthyl]acetamide (78).

Intermediate (±)-71 can be treated with glycine benzyl ester and deprotected to produce (±)-2-(3,4-dichlorophenyl)-N-methyl-N-1-[1,2,3,4-tetrahydro-7-(N-2-acetic acid)-sulfonamido-2-(1-pyrrolidinyl)naphthyl]acetamide (79).

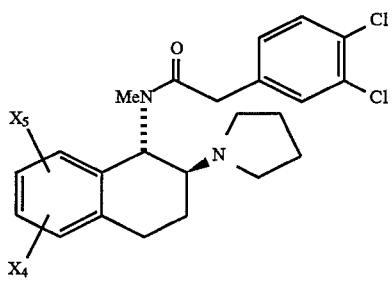

(±)-72, X₅ = —H, X₄ = OCH₂CO₂H
(±)-73, X₅ = —OCH₂CO₂H, X₄ = —H
(±)-74, X₅ = —NHSO₂Me, X₄ = —H
(±)-75, X₅ = —H, X₄ = —NHSO₂Me
(±)-76, X₅ = —H, X₄ = —CONHCH₂CO₂H
(±)-77, X₅ = —H, X₄ = —SO₂NHCH₂CO₂H
(±)-78, X₅ = —CONHCH₂CO₂H, X₂₄ = —H
(±)-79, X₅ = —SO₂NHCH₂CO₂H, X₄ = —H

The compounds of formula III of the present invention are prepared by substituting the central phenyl ring with polar groups.

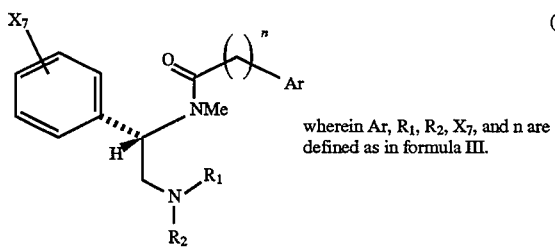

wherein Ar, $R_1$, $R_2$, $X_7$, and n are defined as in formula III.

Compound 80 and analogues undergo a variety of diazonium-involving reactions for the attachment of polar groups (Scheme 7).

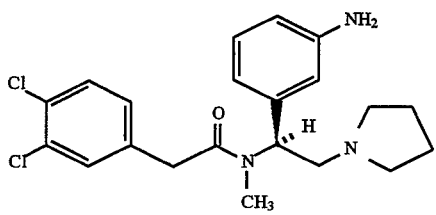

Using the procedure shown in Scheme 7, the following compounds are made.

Intermediate 81 can be treated with dibenzyl phosphoryl chloride followed by deprotection to produce 2-(3,4-dichlorophenyl)-N-methyl-N-{1-3-(O-phosphoryl) hydroxyphenyl-2-(1-pyrrolidinyl)ethyl}acetamide (87).

Intermediate 85 can be coupled to methanesulfonyl chloride to produce 2-(3,4-dichlorophenyl)-N-methyl-N-{1-[3-(N-methanesulfonamido)aminomethyl]phenyl-2-(1-pyrrolidinyl)ethyl}acetamide (88).

Intermediate 85 can be coupled to 2S-isothiocyanato succinic acid and deprotected to produce 2-(3,4-dichlorophenyl)-N-methyl-N-{1-[3-(N-succinic acid-2S-thioureido)aminomethyl]phenyl-2-(1-pyrrolidinyl)ethyl}acetamide (89).

Intermediate 80 can be treated with dibenzyl phosphoryl chloride followed by deprotection to produce 2-(3,4-dichlorophenyl)-N-methyl-N-{1-3-(N-phosphoramido) aminophenyl-2-(1-pyrrolidinyl)ethyl}acetamide (90).

87, R = —OPO₃H₂
88, R = —CH₂NHSO₂Me
89, R = (S)—CH₂NHC(S)NHCH(CO₂H)CH₂CO₂H
90, R = —NHPO₃H₂

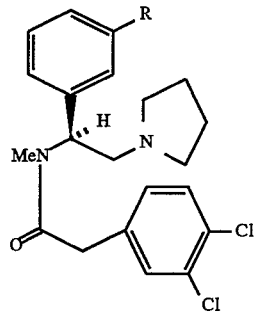

The compounds of formula IV may be prepared by Scheme 8.

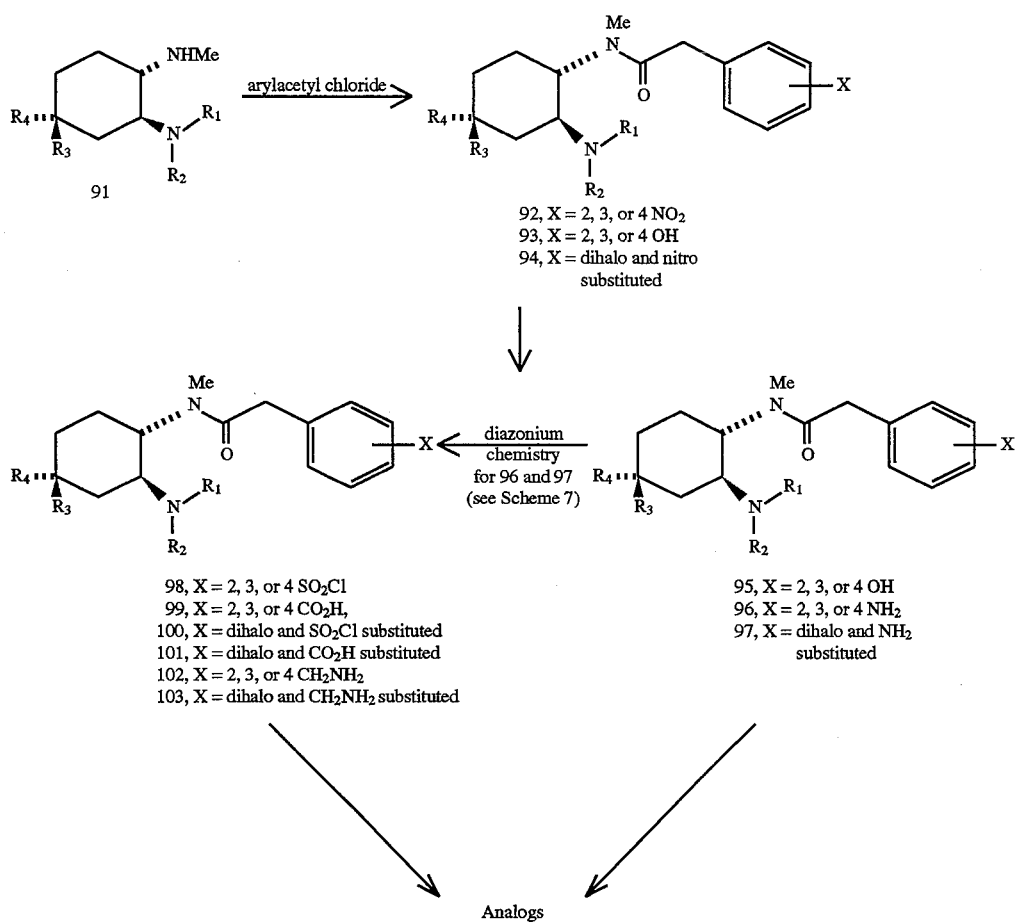

wherein $R_1$, $R_2$, $R_3$, and $R_4$ are defined in formulas III and IV.

The diamino intermediate 91 (J. Med. Chem. 1990, 33, 286) can be coupled to different regioisomers of nitrophenylacetic acid, which are all commercially available. Reduction of the nitro group provides an amino group for the attachment of polar groups. Alternatively, the amino intermediates 95–97 readily undergo diazonium chemistry that converts the amino groups to carboxyl and sulfonyl chloride groups. This allows the polar groups to be attached via different linkers.

Following the procedure in Scheme 8, the following compounds are made.

Intermediate 96 can be treated with methanesulfonyl chloride to produce (−)-(5α,7α,8β)-N-methyl-N-[7-(1-pyrrolidinyl)-1-oxaspiro-[4,5]dec-8-yl]-3-(N-methanesulfonamido)aminophenylacetamide (104).

Intermediate 98 can be coupled to glycine benzyl ester and deprotected to yield (−)-(5α,7α,8β)-N-methyl-N-[7-(1-pyrrolidinyl)-1-oxaspiro-[4,5]dec-8-yl]-3-(N-2acid) sulfonamidophenylacetamide (105).

Intermediate 99 can be coupled to glycine benzyl ester and deprotected to yield (−)-(5α,7α,8β)-N-methyl-N-[7-(1-pyrrolidinyl)-1-oxaspiro-[4,5]dec-8-yl]-3-(N-2-acetic acid)carboxamidophenylacetamide (106).

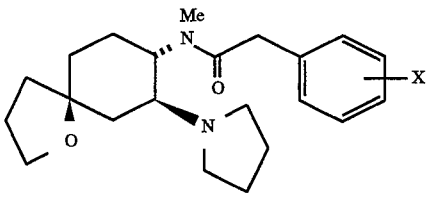

104, X = NHSO$_2$CH$_3$,
105, X = SO$_2$NHCH$_2$CO$_2$H
106, X − CONHCH$_2$CO$_2$H

Compounds of the above formulas may have one or more asymmetric carbon atoms. Pure sterochemically isomeric forms of the above compounds may be obtained, and diastereoisomers isolated by physical separation methods, including, but not limited to crystallization and chromatographic methods. Cis and trans diasteriomeric racemates may be further resolved into their isomers. If separated, active isomers may be identified by their activity. Such purification is not, however, necessary for preparation of the compositions or practice of the methods herein. As used herein, the compounds provided herein also include pharmaceutically acceptable salts, acids and esters thereof, stereoisomers, and also metabolites or prodrugs thereof that possess activity as analgesics but do not cause substantial CNS effects when administered or applied. Metabolites include any compound that is produced upon administration of the compound and metabolism thereof.

In a composition aspect, the kappa agonist compounds of the present invention are formulated into parenteral, local and topical formulations.

The compositions are formulated as injectables, as oral and rectal formulations for systemic administration, and for local and topical administration as creams, aqueous or non-aqueous suspension, lotions, emulsions, suspensions or emulsions containing micronized particles, gels, foams aerosols, solids and other suitable vehicles for application to the skin, eyes, lips and mucosa, as suppositories or cream for vaginal administration, and as combinations with bandages, patches, bioadhesives and dressings. The compounds may be formulated in combination with other agents, such as local anesthetics and other therapeutic agents. The other agents may be mixed in the compositions are provided and administered prior to, simultaneously with or subsequent to administration of the compositions provided for the methods herein. Such agents include, but are not limited to: antibiotics, including cephalosporins, β-lactams, tetracyclines, vancomycins, sulfas and aminoglycosides; antivirals, including acylovir; and antifungals including clotrimazole.

In a method aspect the present invention provides method to treat hyperalgesia by applying an mount of a compound or composition to a mammal to ameliorate or eliminate pain. Thus, the method of the present invention comprises a method of treating pain internally or externally present in the mammalian body including: internal injuries, such as caused by accident or surgical procedures; abnormal functioning of body organs; irritation associated with intimation following local infection, blisters, boils, or acute skin injuries, such as abrasions, burns, sunburn, superficial cuts, surgical incisions, toothaches, contusions, irritations, inflammatory skin conditions, including but not limited to poison ivy, and allergic rashes and dermatitis and any condition that yields a hyperalgesic pain state and other such conditions.

Assessment of Anti-hyperalgesic Activity

The pharmacological activity of the compounds of the present invention may be assessed by several art-recognized in vitro and in vivo models. Some of the typical models are described herein.

(a) Inflamed knee joint hyperalgesia model and blood pressure response to compression of the inflamed knee joint Intimation in a joint is often associated with hyperalgesia [pain during normal flexion and extension and during the application of gentle innocuous pressure] and/or persistent pain [resting pain; Schaible et al. (1993) Pain 55: 5–54]. During the course of knee joint intimation, a cascade of events occurs, which includes: (i) synthesis and release of inflammatory mediators in the joint, (ii) release of neuropeptides from afferent fibers in the joint cavity, and (iii) increased primary afferent outflow from group II, III, IV sensory fibers [Schaible et al. (1993) Pain 55: 5–54]. An important result of this cascade is that there is an augmentation in the response of small, lightly myelinated and unmyelinated afferents to low intensity stimuli. In this manner, the peripheral nerve innervating inflamed tissue can evoke an exaggerated behavioral response to otherwise innocuous stimuli, i.e., a state of hyperalgesia. Thus, intimation of the knee joint will result in increased spontaneous afferent activity, the appearance of an exaggerated discharge with joint flexion and extension [Schaible et al. (1995) J. Neurophysiol. 54:1109–1122] and signs of a pain-associated autonomic reaction [Sata et al (1984) Neurosci. Lett. 52: 55–60].

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight beating, suggesting an ongoing pain state. According to electrophysiological studies, in the course of the development of this acute arthritis, C and A$\delta$ units normally responding only to extreme joint distortion become activated by slight movement [Schaible et al. (1985) J. Neurophysiol. 54:1109–1122]. Spinal neurons with knee joint receptive fields in the deep dorsal horn of the spinal cord show clear development of hyperexcitability with the acute inflammation in the joint [Neugebauer et al. (1993) J. Neurosci. 70: 1365–1377]. This sensitization of group III and IV fibers was observed within 2–3 hours after injection of kaolin and carrageenan into the knee joint, a time course that closely matches the time course of the development of hyperalgesia in the rat knee joint compression model. These observations indicate that spinal cord neurons and joint primary afferent fibers become sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle [Williamson et al. (1994) J. Physiol. 475: 351–357]. This response is dependent on the changes in intramuscular pressure and the quality of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and A units was observed in the rat gastrocnemius muscle by infiltration with carrageenan [Handwerker et al. (1991) Pain and Inflammation, Proceeding of the VIth World Congress on Pain, Bond et al. eds., Elsevier Science Publishers BV, pp. 59–70]. Based on these considerations, it appears that compression of the inflamed knee joint yields a noxious stimulus and this in mm activates a sympathetic response resulting in an increase in BP.

Local inflammation of the knee results in a state where otherwise innocuous stimuli results in a prominent autonomic response, including increased blood pressure (BP) and heart rate [see, e.g., Sata et al (1984) Neurosci. Lett. 52: 55–60]. Alternatively, neural outflow from the inflamed knee is recorded [see, e.g. Neugebauer et al (1993) J. Neurosci. 70: 1365–1377].

An in vitro test that measures spontaneous discharge in injured skin by topical application may also be used. [see, e.g., Andreev et al. (1994) Neurosci. 58: 793–798].

(b) Formalin-induced nociception

Administration of formalin into the paw results in a localized inflammation and a pain response that is moderate in intensity and continuous in duration. Unlike many other assays of nociception, the formalin assay measures tonic pain that is a result of tissue injury, and therefore is a model which is more relevant to clinical pain states in humans [see Tjolsen et al. (1992) Pain 51: 5–17]. In the rat the response to formalin-induced pain consists of spontaneous flinching behavior, characterized by paw lifting and paw shaking, and a rapid vibration of the paw after drawing it under the body. The flinching response can be reliably quantitated and exhibits two peaks of activity which are indicative of acute and tonic pain [Wheeler-Aceto and Cowan (1991) *Psychopharmacology* 104: 35–44]. The early or acute phase lasts from 0–5 min post-formalin and is followed by a quiescent period lasting approximately 15 min. The tonic phase occurs from 20–35 mitt following formalin injection and is the interval where the number of flinching responses is maximal. This model has been characterized in several species [Tjolsen et al. (1992) *Pain* 51: 5–17] and is sensitive to the analgesic effects of opiates administered by a variety of routes, including local administration directly into the paw. In addition, the test is particularly sensitive to the effects of κ agonists [Wheeler-Aceto and Cowan (1991) *Psychopharmacology* 104: 35–44].

Inflammation is induced by subcutaneous injection of 50 μl of a 5% formalin solution into the dorsal surface of the right hind paw of male Sprague-Dawley rats weighing 70–90 g. Injections of drug are given into the dorsal surface of the paw prior to formalin injection, and flinching behavior is quantitated by counting the number of responses that occur during the tonic phase of pain, lasting from 20–35 rain after formalin injection. Results are expressed as the mean percent antagonism of formalin-induced flinching calculated for individual drug-treated, formalin-injected rats using the following formula:

$$\frac{(\text{mean formalin response} - \text{mean saline response}) - \text{individual response}}{\text{mean formalin response} - \text{mean saline response}} \times 100$$

The mean formalin response is the mean behavioral score of vehicle-treated and formalin-injected rats. The mean saline response is the pooled behavioral score from rats injected with 50 μl of saline into the paw.

(c) Randall-Selitto Test

Numerous variations and exemplifications of this assay are known to those of skill in this art [see, Randall et al (1957) *Arch. Int. Pharmacodyn*.111: 409–419; see, also, e.g., U.S. Pat. No. 5,434,292, U.S. Pat. No. 5,369,131, U.S. Pat. No. 5,345,943, U.S. Pat. No. 5,242,944 and U.S. Pat. No. 5,109,135.

The pain threshold is measured in this method as the amount of pressure in g required to induce a flight reaction (struggle) when applied to the foot of an experimental animal exhibiting hyperalgesia, typically an inflamed paw, compared to a control, such as the same or equivalent animal in the absence of the intimation, and/or in the absence of a test compound. Incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined.

Stein and coworkers [Stein et al. (1988) *Pharmacol. Biochem. Behav.* 31:445–451; Stein et al. (1989) *J. Pharmacol. Exp. Ther.* 248: 1269–1275] have developed a model of peripheral intimation and hyperalgesia in rats, which supports the role of opiates in mediating peripheral analgesia. In this protocol, modified Freund's adjuvant is used as the inflammatory stimulus, and the paw pressure test is used to assess the response of the rat to a painful pressure stimulus. The model is sensitive to opiate agonists of the μ, δ and κ subtypes, which produce analgesia upon administration [Antonijevic et al. (1995) *J. Neurosci.* 15: 165–172; Stein et al. (1988) *Neurosci. Lett.* 84: 225–228; Stein et al. (1989) *J. Pharmacol. Exp. Ther.* 248: 1269–1275]. Histological verification of opiate receptor localization and density have confirmed that peripheral opiate receptors are accessible on primary afferent nerve fibers and are upregulated following intimation [Hassan et al. (1993) *Neuroscience* 55:185–193; Przewlocki et al. (1992) *Neuroscience* 48:491–500].

Experiments are conducted in rats weighing 150–250 g at the time of inoculation. Modified Freund's complete adjuvant (FCA) is used as the inflammatory stimulus. Rats are administered an i.pl. injection of the FCA suspension into the right hind foot. Hyperalgesia and antinociception are evaluated using the paw pressure test. The rat is gently restrained and incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. A cutoff pressure of 250 g is used to avoid undue stress and pain to the animal. Baseline responding is established by determining the average of three consecutive trials separated by 10 sec. The same procedure is conducted on the contralateral side and the sequence of sides is alternated between animals to control for order effects. Typically injections are not made in the contralateral (noninflamed) paw; however, in selected cases drugs may be administered to the contralateral paw to evaluate the potential for drug effects in the absence of inflammation.

Analgesic activity is determined by expressing the increase in PPT resulting from the effect of the drug as a percentage of basal preinjection thresholds.

Hyperalgesia can also be produced by inflammatory stimuli such as yeast or carrageenan, endogenous inflammatory mediators such as bradykinin or prostaglandins, or other types of chemical irritants [see Hargreaves and Joris (1993) *APS Journal* 2:51–59].

(d) Acetic acid-induced writhing

This test identifies novel agents which exhibit peripheral analgesic activity against visceral or chemical pain [see Barber and Gottschlich (1986) *Med. Res. Rev.* 12: 525–562; Ramabadran and Bansinath (1986) *Pharm. Res.* 3: 263–270]. Injection of acetic acid into the peritoneal cavity is used as the noxious stimulus, and the number of writhing responses that occur in response to acetic acid are counted in order to quantify the response to pain. Compounds which possess analgesic activity reduce the number of writhing responses that occur. Opiate agonists of the μ and κ subtype exhibit analgesic activity in this model [Barber and Gottschlich (1986) *Med. Res. Rev.* 12: 525–562; Millan (1990) *Trends Pharmacol. Sci.* 11: 70–76]. Novel compounds which demonstrate potency and efficacy in this assay are potential drugs for the treatment of various pathological conditions involving peripheral pain.

The writhing assay is adapted from the procedure originally described by Taber et al. [(1969) *J. Pharmacol. Exp. Ther.* 169: 29–38], using male CF-1 mice weighing 20–25 g. Animals are treated with various doses of drugs prior to the administration of an i.p. injection of 0.6% acetic acid solution. Mice are then placed into observation chambers and the number of writhing responses, as defined by a full hindlimb extension and retraction, are recorded.

The mean number of writhing responses is calculated for vehicle-treated control mice, and the percent inhibition (% I) of writhing is calculated for each mouse that is treated with drug using the following formula:

$$\%I = 100 \times \frac{\text{(mean control writhing responses} - \text{individual test responses)}}{\text{mean control writhing responses}}$$

(e) Hyperalgesia induced by tape stripping

The objective of this assay is to identify novel agents which exhibit peripherally-mediated analgesia in circumstances, such as burns and abrasions, which lead to hyperalgesia. In such injuries, the loss of the stratum corneum is followed by an inflammatory response (erythema) and a painful response to otherwise innocuous stimuli. Removal of the stratum corneum by repeated application and removal of cellophane tape, termed tape stripping, has been shown to be a simplified model of these injuries, which share characteristics of first degree burns [see Flynn (1985) *Percutaneous Absorption*, R. L. Bronaugh and H. I. Maibach, eds., Marcel Dekker Inc., pp. 18–42]. This method of barrier disruption avoids the application of potentially toxic chemicals and permits evaluation of peripheral analgesics following topical administration because tape stripping removes the barrier to effective topical therapy (the stratum corneum) while simultaneously resulting in inflammation and hyperalgesia. Tape stripping has been validated in humans as a model for the testing of topical agents [Pershing et al. (1994) Antimicrob. Agents Chemother. 38: 90–95; Roy and Flynn (1990) *Pharm. Res.* 7: 842–847].

Experiments are conducted in male Sprague-Dawley rats weighing 250–500 g at the time of treatment. After anesthesia of the rat with ketamine-xylamine, a 1–3 $cm^2$ patch of rat skin is treated by repeated application and removal of tape. This procedure results in removal of the stratum corneum as determined by a glistening appearance of the skin. The tape stripped skin is evaluated for a visible erythema and for sensitivity to contact by heat or pressure stimuli using a focused beam of light, by testing in the paw pressure apparatus or by touch with von Frey hairs. The diameter of the von Frey hairs will be selected based on a diameter which causes no response in control rats but has a readily detectable response in treated rats.

Typically analgesics will be formulated in a suitable topical medium and applied to the treated skin. Some rats will receive only the topical medium without analgesic to control for an effect of the topical medium alone. The presence of analgesia is determined by the latency to respond to the heat stimulus or by response to touch or pressure.

FORMULATIONS OF THE PRESENT INVENTION

Effective concentrations of one or more of the compounds of the present invention or pharmaceutically acceptable derivatives thereof are mixed with a suitable pharmaceutical carrier or vehicle for systemic, topical or local administration. Compounds are included in an mount effective for reducing the hyperalgesic state or other symptoms for which treatment is contemplated. The concentration of active compound in the composition will depend on absorption, inactivation, excretion rates of the active compound, the dosage schedule, and mount administered as well as other factors known to those of skill in the art. For topical and local administration, the dosages are higher, typically at least about 5 to 10 fold, than the mount delivered when administered systemically orally.

The compounds of the present invention possess analgesic activity and can be used for the relief of pain without loss of consciousness. For example, compounds can be used to treat muscle spasm, arthritis and other musculoskeletal conditions, e.g., bursitis, relieve mild to moderate postoperative and postpartum pain, dysmenorrhea and pain of traumatic origin. Additionally, the compounds of the present invention can be administered for the treatment of severe pain, e.g., pain associated with adenocarcinoma, amputation of a limb, and third degree burns over a major portion of the body in animals and humans.

Selected compounds of the present invention have activity as narcotic antagonists. They can be used to counteract or prevent excessive central nervous system depression and respiratory depression resulting from the administration of morphine or other morphine-like drags, e.g., hydromorphone, oxymorphone, methadone and meperidine. The compounds are also capable of inducing an abstinence syndrome in narcotic addicted subjects, i.e., induce withdrawal effects for diagnostic purposes.

The dosage of the compound of Formulas I, II, III and IV for analgesic purposes is from about 0.001 to about 20 mg/kg body weight of the patient. The compounds of Formulas I, II, III, and IV are conveniently prepared in 5, 10, 25, 50, 75, 100 and 200 mg dosage units for administration for 1 to 4 times a day. Preferred unit dosages are from 0.05 to 10 mg/kg body weight of the patient.

The compounds are administered orally, parenterally, rectally and topically.

Pharmaceutical carders or vehicles suitable for administration of the compounds and for the methods provided herein include any such carders known to those skilled in the art to be suitable for the particular mode of administration. In addition, the compounds may be formulated as the sole pharmaceutically active ingredient in the composition or may be combined with other active ingredients.

a) Systemic Formulations

The formulations of the present invention are provided for administration to humans and animals in unit dosage forms, such as tablets, capsules, pills, powders, granules, sterile parenteral solutions or suspensions, and oral solutions or suspensions, and oil-water emulsions containing suitable quantities of a compound of Formulas I, II, III, and IV or pharmacologically acceptable salts thereof.

Pharmaceutical dosage unit forms are prepared to provide from about 0.05 mg to about 500 mg and preferably from about 1.0 to about 200 mg of the essential active ingredient or a combination of essential ingredients per dosage unit form.

Oral pharmaceutical dosage forms are either solid or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Pharmaceutically acceptable carders utilized in tablets are binders, lubricants, diluents, disintegrating agents, coloring agents, flavoring agents, and wetting agents. Enteric-coated tablets, due to their enteric-coating, resist the action of stomach acid and dissolve or disintegrate in the neutral or alkaline intestines. Sugar-coated tablets are compressed tablets to which different layers of pharmaceutically acceptable substances have been applied. Film-coated tablets are compressed tablets which have been coated with a water soluble polymers. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Examples of binders include glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Disintegrating agents include corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumia hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in water or water-in-oil.

Elixirs are dear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic adds and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

Parenteral administration of the formulations of the present invention includes intravenous, subcutaneous and intramuscular administrations.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Pharmaceutically acceptable carders used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule or a syringe with a needle.

All preparations for parenteral administration must be sterile, as is know and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The pharmaceutically therapeutically active compounds of Formulas I, II, III and IV are administered orally, parenterally or rectally in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof.. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses which are not segregated in packaging.

Compounds of the present invention in formulations may be included with other active compounds to obtain desired combinations of properties. Other active compounds with known pharmacological properties include analgesics such as aspirin, phenacetin acetaminophen, propoxyphene, pentazocine, codeine, meperidine, oxycodone, mefenamic add, and ibuprofen; muscle relaxants such as methocarbamol, orphenadrine, carisoprodol, meprobamate, chlorphenesin carbamate, diazepam, chlordiazepoxide and chlorzoxazone; analeptics such as caffeine, methylphenidate and pentylenetetrazol; corticosteroids such as methylprednisolone, prednisone, prednisolone and dexamethasone; antihistamines such as chlorpheniramine, cyproheptadine, promethazine and pyrilamine.

b) Local and Topical Formulations

Typically a therapeutically effective dosage is formulated to contain a concentration of at least about 0.1% w/w up to about 50% w/w or more, preferably more than 1% w/w of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the hyperalgesic or other condition and may be empirically determined.

Compounds are typically included at concentrations 0.001% w/w or greater than 1% w/w up to 50% w/w or higher. The concentration is generally greater than the concentration for systemic administration of the compound. Preferable concentrations are in the range of 0.01% w/w to about 25%w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, or any other formulations suitable for topical or local administration.

The route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection.

Pharmaceutical and cosmetic carders or vehicles suitable for administration of the compounds provided herein include any such carders known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an anti-hyperalgesic effective amount of one or more of the compounds selected as described herein, in an effective concentration range [by weight], between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1% w/w, more preferably 2% w/w.

To formulate a composition, the weight fraction of compound is dissolved, suspended, dispersed or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, skin penetration enhancers, coloring agents, fragrances, emulsifiers, thickening agents, and solvents.

For local internal administration, such as intra-articular administration, the compounds are preferably formulated as a suspension in an aqueous-based medium, such as isotonically buffered saline or are combined with a biocompatible support or bioadhesive intended for internal administration.

Lotions

The lotions contain an effective concentration of one or more of the compounds. The effective concatenation is preferably effective to deliver an anti-hyperalgesic amount, typically at a concentration of between about 0.1–50% w/w or more of one or more of the compounds provided herein. The lotions also contain from 1% to 50% w/w, preferably from 3% to 15% w/w of an emollient and the balance water, a suitable buffer, a $C_2$ or $C_3$ alcohol, or a mixture of water of the buffer and the alcohol. Any emollients known to those of skill in the art as suitable for application to human skin may be used. These include, but are not limited to, the following:

(a) Hydrocarbon oils and waxed, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil and soybean oil.

(d) Acetoglyceride esters, such as acetylated monoglycerides.

(e) Ethoxylated glycerides, such as ethoxylated glyceryl monostearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to pelargonic, lauric, myristic, palmitic, stearic, isostearic, hydroxystearic, oleic, linoleic, ricinoleic, arachidonic, behenic, and erucic acids.

(i) Fatty alcohols having 10 to 20 carbon atoms, such as but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to, ethoxylated fatty alcohols of 10 to 20 carbon atoms, such as, but are not limited to, the lauryl cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly)ethylene oxide) homopolymers [M.W. 100,000–5,000,000], polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and all-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain from 1% w/w to 10% w/w, more preferably from 2% w/w to 5% w/w, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and all-fatty acid esters of ethylene oxides mono- and di-fatty acid esters of ethylene glycol wherein the fatty add moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably, the compound, is dissolved, suspended or otherwise uniformly dispersed in the mixture.

Other conventional components of such lotions may be included. One such additive is a thickening agent at a level from 1% to 10% w/w of the composition. Examples of suitable thickening agents include, but are not limited to: cross-linked carboxypolymethylene polymers, ethyl cellulose, polyethylene glycols, gum, tragacanth, gum kharaya, xanthan gums and bentonite, hydroxyethyl cellulose, and hydroxypropyl cellulose.

Creams

The creams are formulated to contain concentration effective to deliver an anti-hyperalgesic effective amount of the compound to the treated tissue, typically at between about 0.1%, preferably at greater than 1% up to and greater than 50%, preferably between about 3% and 50%, more preferably between about 5% and 15% of one or more of the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

Solutions and suspensions for topical and local administration

The solutions are formulated to contain an amount of one or more compounds effective to deliver an anti-hyperalgesic amount, typically at a concentration of between about 0.1–50% w/w, preferably at least more than 1% w/w, more preferably more than 2% w/w of one or more of the compounds provided herein. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol and mixtures thereof. Such solvent systems earl also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic add and sodium bisulfite; chelating agnets, such as ethylenediaminetetraacetic acid [EDTA]; buffers, such as acetates, citrates and phosphates; and agents for the adjustment of tonicity such as sodium chloride or dextrose. Liquid preparations can be enclosed in ampoules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or may be formulated as an aerosol or foam and applied to the skin as a spray-on. The aerosol compositions typically contain from 25% to 80% w/w, preferably from 30% to 50% w/w, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspension may also be topically applied to the eyes and mucosa. Solutions, particularly those intended for opthalmic use, may be formulated as 0.01%–10% w/w isotopic solutions, pH about 5–7, with appropriate salts, and preferably containing one or more of the compounds herein at a concentration of about 0.1% w/w preferably greater than 1% w/w, up to 50% w/w or more. Suitable opthalmic solutions are known [see, e.g. U.S. Pat. No. 5,116,868, which describes typical compositions of opthalmic irrigation solutions and solutions for topical application]. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium titrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The active compounds of the present invention can also be mixed with other active materials, that do not impair the desired action, or with materials that supplement the desired action, including viscoelastic materials, such as hyaluronic add, which is sold under the trademark HEALON [solution of a high molecular weight (MW of about 3 million) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803], VISCOAT [fluorine-containing (meth) acrylates, such as, 1H, 2H, 2H-heptadecafluorodecylmethacrylate; see, e.g., U.S. Pat. Nos. 5,278,126, 5,273,751 and 5,214,080; commercially available from Alcon Surgical, Inc.], ORCOLON [see, e.g., U.S. Pat. Nos. 5,273,056; commercially available from Optical Radiation Corporation], methylcellulose, methyl hyaluronate, polyacrylamide and polymethacrylamide [see, e.g., U.S. Pat. No. 5,273,751]. The viscoelastic materials are present generally in mounts ranging from about 0.5 to 5.0% w/w, preferably 1 to 3% w/w of the conjugate material and serve to coat and protect the treated tissues. The compositions may also include a dye, such as methylene blue or other inert dye, so that the composition can be seen when injected into the eye or contacted with the surgical site during surgery.

Gels

Gel compositions can be formulated by simply admixing a suitable thickening agent to the previously described solution or suspension composition. Examples of suitable thickening agents have been previously described with respect to the lotions.

The gelled compositions contain an effective amount of one or more of an antihyperalgesic amount, typically at a concentration of between about 0.1–50% w/w or more of one or more of the compounds provided therein; from 5% to 75% w/w, preferably from 10% to 50% w/w, of an organic solvent as previously described; from 0.5% to 20% w/w, preferably from 1% to 10% w/w of the thickening agent; the balance being water or other aqueous carrier.

Solids

Compositions of solid forms may be formulated as stick-type compositions intended for application to the lips or other parts of the body. Such compositions contain an effective amount of one or more of the compounds provided therein. The amount is typically an amount effective to deliver an anti-hyperyperalgesic amount, typically at a concentration of between about 0.1–50% w/w or more of one or more of the compounds provided herein. The solids also contain from about 40% to 98% w/w, preferably from about 50% to 905 w/w, of the previously described emollients. This composition can further contain from 1% to 20% w/w, preferably from 5% to 15% w/w, of a suitable thickening agent, and, if desired or needed, emulsifiers and water or buffers. Thickening agents previously described with respect to lotions are suitably employed in the composition in solid form.

Other ingredients such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

Additional ingredients

Other active ingredients include, but are not limited to, antibiotics, antivirals, antifungals, anti-inflammatories, including steroidal and non-steroidal anti-inflammatories, anesthetics and mixtures thereof. Such additional ingredients include any of the following:

a. Antibacterial agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof; such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-β, Chloramine-T, Dichloramine-T, Formosulfathiazole, $N^2$-Formyl-sulfisomidine, $N^4$-β-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Surfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Surlamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N, N'digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibornol.

c. Antifungal (antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antigungal (synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma agents

Antiglaucoma agents, such as Dapiprazoke, Dichlorphenamide, Dipivefrin and Pilocarpine.

f. Anti-inflammatory agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Acid;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Sal;icylate, Mesalamine, 1-Naphthyl Salicylate, Olsalazine and Sulfasalazine;

Thiazinecarboxamides such as Droxicam, Isoxicam and Piroxicam;

Others such as ε-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4, 6-ditertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bornyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexaehlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline;

Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

Combinations and kits

The compounds and compositions containing the compounds may also be coated on bandages, mixed with bioadhesives or included in dressings. Thus, combinations of bandages, bioadhesives, dressings and other such materials and the compositions formulated as described herein are provided. Kits containing these combinations, which may also include compositions containing the above listed agents, are also provided.

Articles of manufacture

The compounds and compositions provided herein may be packaged as articles of manufacture containing packaging material, one or more of the compounds provided herein, which is effective for ameliorating peripheral hyperalgesia, within the packaging material, and a label that indicates that the compound, N-oxide, acid, salt or other derivative thereof is used for treating hyperalgesic conditions.

Methods of treatment

Compositions for use with human skin preferably may be applied at least once per day, or if necessary, to achieve the desired result, more often, to the areas of the skin for which treatment is sought. It is understood that the precise treatment regimen depends upon the individual treated and may be ascertained empirically depending upon the formulation, and particularly, the age of the treated individual. Any regimen is acceptable as long as the desired antihyperalgesic effects are achieved without substantial deleterious or sustained undesirable side effects.

The methods for treating human skin are practiced by applying to the skin, preferably at least daily, a composition suitable for human skin treatment or treatment of mucosal membranes and other body surface tissues, including the vagina, rectum, mouth, eyes and other such tissues. The compositions may be injected into joints or other inflamed areas.

Compositions may be combined with bandages, bioadhesives and other dressings and applied to the body in combination therewith.

The following examples are included for illustrative purposes only and are not intended to limit the scope of the invention.

Example A—Capsules

| Active Compound | 2.5 gm |
|---|---|
| Corn starch | 23.0 gm |
| Lactose | 145.0 gm |
| Talc | 15.0 gm |
| Magnesium stearate | 3.0 gm |

The ingredients were mixed and were encapsulated using techniques practiced in the art.

Example B—Tablet

| Active Compound | 150 gm |
|---|---|
| Lactose | 125 gm |
| Corn starch | 50 gm |
| Magnesium stearate | 2.0 gm |
| Liquid Petrolatum | 2.0 gm |

The ingredients were mixed, then put through U.S. Standard Screens to produce fine granules. The granules were compressed into tablets, each tablet containing about 150 mg of an active compound of the present invention.

Example C—Syrup

| Active Compound | 25 gm |
|---|---|
| Lemon Oil | 2 ml |
| Sucrose | 650 gm |
| Citric Acid | 4 gm |
| Benzoic Acid | 3 gm |
| Tragacanth | 16 gm |
| Deionized water q.s. | 1000 ml |

The ingredients, without the active compound, are dispersed in water to make about 800 to 900 ml of solution. The active compound is then added and the solution is stirred into a syrup. Water is then added to make 1000 ml of the syrup.

Example D—Parenteral Solution

| Active Compound | 30 gm |
|---|---|
| Methylparaben | 3 gm |
| Propylparaben | 1 gm |
| Lidocaine | 5 gm |
| Deionized water q.s. | 1000 ml |

The ingredients are dissolved in water to provide a solution followed by sterilization by filtration.

Example E—Rectal Suppository

| Active Compound | 80 gm |
|---|---|
| Propylene glycol | 95 gm |
| Polyethylene glycol 4000 | 1800 gm |

The active compound is added to the propylene glycol and milled until a finely divided uniform mixture is formed. The polyethylene glycol 4000 is melted and the propylene glycol dispersion is added with stirring to obtain a suspension. The suspension is poured into molds, allowed to solidify and removed from the molds for packaging.

47

Example F—Water-washable ointment

| Active Compound | 1.4% w/w |
|---|---|
| Lanolin alcohol | 0.15% w/w |
| Emulsifying wax NF | 7.5% w/w |
| PEG-20 glycerides | 5.0% w/w |
| Petrolatum | 86.0% w/w |

The ingredients are melted together and mixed well until the resulting ointment congeals.

Example G—Oil-in-Water Cream

| Active Compound | 10.0% w/w |
|---|---|
| Benzyl alcohol | 4.0% w/w |
| Propylene glycol | 10.0% w/w |
| Polyethylene glycol 400 | 10.0% w/w |
| Petrolatum | 20.0% w/w |
| Stearyl alcohol | 10.0% w/w |
| Poloxamer | 10.0% w/w |
| Water q.s. | 100 |
| Buffer to pH | 7.0% w/w |

In preparing the oil-h-water cream, water, propylene glycol and polyethylene glycol 400 are heated to about 70 to 80_C., followed by adding a mixture of petrolatum, stearyl alcohol and poloxamer and the mixture is stirred until homogeneous. The active compound in benzyl alcohol is added and the mixture is homogenized. The pH is then adjusted with a buffer to about 7.0.

Example H—Aqueous Gel

| Active Compound | 10.0% w/w |
|---|---|
| Benzyl alcohol | 4.0% w/w |
| Hydroxyethyl cellulose | 3.0% w/w |
| Water q.s. | 100 |
| Buffer to pH | 7.0% w/w |

The aqueous gel is prepared by mixing the active compound, benzyl alcohol and adding the mixture to buffered water. Hydroxyethyl cellulose is then added with stirring until the mixture gels.

Having described the invention with reference to its preferred embodiments, it is to be understood that modifications within the scope of the invention will be apparent to those skilled in the art.

What is claimed is:

1. A compound of the formula I or a pharmaceutically acceptable salt thereof (I)

wherein n is 1–3;

$R_1$ and $R_2$ are independently —$CH_3$; —$(CH_2)_m$, where m is 4–8; —$CH_2CH(OH)(CH_2)_2$—; —$CH_2CH(F)(CH_2)_2$—; —$(CH_2)_2O(CH_2)_2$—; or —$(CH_2)_2CH=CHCH_2$—;

48

Ar is unsubstituted or mono-, or di-substituted phenyl wherein said substituents are selected from the group consisting of halogen, $OCH_3$, $SO_2CH_3$, $CF_3$, amino, alkyl, and 3,4-dichloro; benzothiophenyl; benzofuranyl; naphthyl; diphenyl methyl; or 9-fluorene;

Z is

—$P(O)(OBn)_2$; —$P(O)(OH)_2$; —$(CH_2)_pC(O)NHOH$; —$(CH_2)_pCO_2H$; —$SO_2CH_3$; —$SO_2NH_2$; —$CO(CH_2)_pCH(NH_2)(CO_2H)$; —$COCH(NH_2)(CH_2)_pCO_2H$; —$CO_2CH_3$; —$CONH_2$; $(CH_2)_pO(CH_2)_pCO_2H$; —$(CH_2)_pO(CH_2)_pCONHOH$; —$(CH_2)_pNHSO_2CH_3$; —$(CH_2)_pNHC(S)NHCH(CO_2H)(CH_2)_pCO_2H$; —$(CH_2)_pSO_3H$; or or Z is wherein p is 0–20;

$R_3$ is —H or —AC;

$X_2$ is —$CO_2H$; —$NHSO_2CH_3$; —$NHP(O)(OBn)_2$; —$NHP(O)(OH)_2$; —$OP(O)(OBn)_2$; or —$OP(O)(OH)_2$,

X and Y are independently

—$CH_2NHSO_2CH_3$; —$CH_2NHP(O)(OBn)_2$; —$CH_2NHP(O)(OH)_2$; —$CH_2OP(O)(OBn)_2$; —$CH_2OP(O)(OH)_2$; —$(CH_2)_qO(CH_2)_qCO_2H$; —$(CH_2)_qO(CH_2)_qSO_3H$; —$(CH_2)_qO(CH_2)_qCHNHOH$; —$CH_2NHC(S)NHCH(CO_2H)(CH_2)_qCO_2H$; or wherein q is 1–20 r is 1–20

$R_4$ is —H or —Ac and $X_3$— is —$CO_2H$; —$NHSO_2CH_3$; —$NHP(O)(OBn)_2$; —$NHP(O)(OH)_2$; —$OP(O)(OBn)_2$; or —$OP(O)(OH)_2$.

2. The compound according to claim 1 selected from the group consisting of: {4-[1-(3,4-Dichlorophenyl)acetyl-2R-(1-pyrrolidinyl)-methyl]piperazinyl}acetic acid; [1-(3,4-Dichlorophenyl)acetyl-4-methanesulfonyl-2R-(1-pyrrolidinyl)methyl]piperazine; [4-S-Aspartic acid-a-amido-1-(3,4-dichlorophenyl)acetyl-2R-(1-pyrrolidinyl) methyl]piperazine; Methyl-[2 R-(O-2-acetic acid) hydroxymethyl-4-(3,4-dichlorophenyl)acetyl-3R-(1-pyrrolidinyl)methyl]-1-piperazinecarboxylate; Methyl-[2R-

(O-S-aspartic acid-a-acetyl)hydroxymethyl-4-(3,4-dichlorophenyl)acetyl-3R-(1-pyrrolidinyl)methyl]-1-piperazinecarboxylate; Methyl-[4-(3,4-dichlorophenyl)acetyl-2R-(N-methanesulfonamido)aminomethyl-3R-(1-pyrrolidinyl) methyl]-1-piperazinecarboxylate; Methyl-{4-[3,4-dichlorophenyl]acetyl-3R-[1-pyrrolidinyl]methyl-2R-[N-(succinic acid-2S-thioureido)]aminomethyl}-1-piperazinecarboxylate; Methyl-[2S-(O-2-acetic acid)hydroxymethyl-4-(3,4-dichlorophenyl)acetyl-5R-(1-pyrrolidinyl)methyl]-1-piperazinecarboxylate; Methyl-[2S-(O-S-aspartic acid-a-acetyl)hydroxymethyl-4-(3,4-dichlorophenyl)acetyl-5R-(1-pyrrolidinyl)methyl]-1-piperazinecarboxylate; Methyl-[4-(3,4-dichlorophenyl)acetyl-2S-(N-methanesulfonamido)aminomethyl-5R-(1-pyrrolidinyl)methyl]-1-piperazinecarboxylate; Methyl-{4-[3,4-dichlorophenyl]acetyl-5R-[1-pyrrolidinyl]methyl-2S-[N-(succinic acid-2S-thioureido)]aminomethyl}-1-piperazinecarboxylate; Methyl-[2R-(O-2-acetic acid)hydroxymethyl-4-(3,4-dichlorophenyl)acetyl-5R-(1-pyrrolidinyl)methyl]-1-piperazinecarboxylate; Methyl-[2R-(O-S-aspartic acid-a-acetyl)hydroxymethyl-4-(3,4-dichlorophenyl)acetyl-5R-(1-pyrrolidinyl)methyl]-1-piperazinecarboxylate; Methyl-[4-(3,4-dichlorophenyl)acetyl-2R-(N-methanesulfonamido)aminomethyl-5R-(1-pyrrolidinyl)methyl]-1-piperazinecarboxylate; and Methyl-{4-[3,4-dichlorophenyl]acetyl-5R-[1-pyrrolidinyl]methyl-2R-[N-(succinic acid-2S-thioureido)]aminomethyl}-1-piperazinecarboxylate.

3. A pharmaceutical composition comprising a compound of claim 1 in a pharmaceutically acceptable carrier.

4. A pharmaceutical composition comprising a compound of claim 2 in a pharmaceutically acceptable carrier.

5. A method of treating hyperalgesia in a patient comprising administering to said patient an effective mount of a compound of claim 1.

6. A method of treating hyperalgesia in a patient comprising administering to said patient an effective mount of a compound of claim 2.

7. A method of treating hyperalgesia in a patient comprising administering to said patient an effective mount of a composition of claim 3.

8. A method of treating hyperalgesia in a patient comprising administering to said patient an effective mount of a composition of claim 4.

9. A pharmaceutical composition comprising a compound of claim 1 and an antibiotic, antiviral, antifungal, anti-inflammatory agent or a mixture thereof in a pharmaceutically acceptable carrier.

10. A pharmaceutical composition comprising a compound of claim 2 and an antibiotic, antiviral, antifungal, anti-inflammatory agent or a mixture thereof in a pharmaceutically acceptable carrier.

* * * * *